(12) United States Patent
Crockett

(10) Patent No.: US 7,016,941 B1
(45) Date of Patent: Mar. 21, 2006

(54) WEB-SITE HOST CONSISTENCY ADMINISTRATION AMONG INCONSISTENT SOFTWARE-OBJECT LIBRARIES OF REMOTE DISTRIBUTED HEALTH-CARE PROVIDERS

(76) Inventor: David A. Crockett, 23803 Lawrence 2140, Marionville, MO (US) 65705

( * ) Notice: Subject to any disclaimer, the term of this patent is extended or adjusted under 35 U.S.C. 154(b) by 0 days.

(21) Appl. No.: 10/862,817

(22) Filed: Jun. 7, 2004

Related U.S. Application Data

(63) Continuation of application No. 09/761,362, filed on Jan. 16, 2001, now Pat. No. 6,751,651.

(60) Provisional application No. 60/176,207, filed on Jan. 14, 2000, provisional application No. 60/168,114, filed on Nov. 30, 1999.

(51) Int. Cl.
*G06F 15/13* (2006.01)

(52) U.S. Cl. .................... 709/206; 707/104.1; 715/858

(58) Field of Classification Search ................ 709/206; 707/104.1; 715/858
See application file for complete search history.

(56) References Cited

U.S. PATENT DOCUMENTS

| | | | |
|---|---|---|---|
| 5,226,161 A | 7/1993 | Khoyi et al. | ................ 719/316 |
| 5,421,015 A | 5/1995 | Khoyi et al. | ................ 718/107 |
| 5,517,605 A | 5/1996 | Wolf | ....................... 707/104.1 |
| 5,961,601 A | 10/1999 | Iyengar | ....................... 709/229 |
| 5,966,705 A | 10/1999 | Koneru et al. | ................. 707/6 |
| 6,101,407 A * | 8/2000 | Groezinger | ................. 600/407 |
| 6,115,027 A * | 9/2000 | Hao et al. | .................... 715/858 |
| 6,168,563 B1 | 1/2001 | Brown | ....................... 600/301 |
| 6,397,253 B1 | 5/2002 | Quinlan et al. | ............. 709/227 |
| 6,424,996 B1 * | 7/2002 | Killcommons et al. | ..... 709/206 |
| 6,542,902 B1 * | 4/2003 | Dulong et al. | ........... 707/104.1 |
| 6,603,494 B1 | 8/2003 | Banks et al. | ................ 345/807 |

OTHER PUBLICATIONS

Mark Smith, "This Is In," *Windows2000 Magazine* (Sep. 1, 1997), //www.win2000mag.com/Articles/Index.cfm?ArticleID=521.

"Understanding the ASP Market: An ISV's Guide," Sound Consulting, L.L.C. (Seattle, WA © 1999, 2000), no month, //download2.citrix.com/ctxlibrary/ibusiness/pdf/ISV_Guide_ASPs.pdf.

"ABC's of ASP" and linked "Glossary of Terms," Copyright 2000 Citrix Systems, Inc., no date, //www.citrix.com/.

* cited by examiner

*Primary Examiner*—John Follansbee
*Assistant Examiner*—Jinsong Hu
(74) *Attorney, Agent, or Firm*—Jonathan A. Bay

(57) ABSTRACT

A method of Web-site host consistency administration provides for consistent presentation of data despite presentation on client machines with inconsistent software-object libraries. The host sends screen images which contact the client's onboard DLLs as little as possible. That way, inconsistency problems called binary incompatibilities are avoided. The client is excused from most of the processing load. The client's role is practically limited to displaying the received screens and sending out keystrokes and cursor-moving device inputs. The light role given the client correspondingly shifts more of a load on server-side processing and data storage. Nevertheless, the method provides high assurance the any client sees substantially the same result for the same request despite differences or inconsistencies in software-object libraries onboard the client's machine.

6 Claims, 14 Drawing Sheets

FIG. 3.
(PRIOR ART)

Client Server
Old Application programming
using a Private Network

Server CPU activities

| | | | |
|---|---|---|---|
| 101 | Store | DLL Objects | Secondary memory via DLLs |
| 102 | Store | Full and complex Operating System | Secondary memory via DLLs |
| 103 | Store | Application Source Program | Secondary memory via DLLs |
| 104 | Store | Application Data Access programs | Secondary memory via DLLs |
| 105 | Store | Network programs | Secondary memory via DLLs |
| 106 | Store | Private Network Protocols | Secondary memory via DLLs |
| 107 | | | |
| 108 | | | |
| 109 | Store | Application Data | Secondary memory via DLLs |
| 110 | Store | Application First stage object with DLL references | Secondary memory via DLLs |
| 111 | Execute | Operating System  example  Microsoft | Primary memory and Secondary memory via DLLs |
| 112 | Execute | Network program using Private network protocols | Network card |
| 113 | | | |
| 114 | Receive | Request from Client | Network card |
| 115 | Analyze | Request | Primary memory via DLLs |
| 116 | Select | Requested Application First stage compile object and linked DLL object references |
| | | | Primary memory and Secondary memory, via DLLs |
| 117 | Select | Requested Data | Primary memory and Secondary memory, via DLLs |
| 118 | Transmit | Requested Application First stage object with DLL references |
| | | | Network card |
| 119 | Transmit | Requested Application Data | Network card |
| 120 | | | |
| 121 | | | |
| 122 | | | |
| 123 | | | |
| 124 | | | |
| 125 | | | |
| 126 | Store | keystrokes/mouse clicks | Interface card and Primary memory |
| 127 | Receive | keystrokes/mouse clicks | Network card and Primary memory |
| 128 | Analyze | keystrokes/mouse clicks | Primary memory via DLLs |

FIG. 4.
(PRIOR ART)

Client Server
Old Application programming
using a Private Network

Client CPU activities

201 Store  DLL* Objects                                                              Secondary memory via DLLs*
202 Store  Full and complex Operating System                                         Secondary memory via DLLs*
203
204 Store  Application Data Access programs                                          Secondary memory via DLLs*
205
206 Store  Network program                                                           Secondary memory via DLLs*
207 Store  Private Network Protocols                                                 Secondary memory via DLLs*
208
209 Store  Requested Application Data set                                            Secondary memory via DLLs*
210 Store  Application First stage object with DLL references                        Secondary memory via DLLs*
211 Execute Operating System   example  Microsoft                                    Primary memory and Secondary memory via DLLs*
212
213 Execute Network program using private network protocols                          Network card
214
215 Send Request for program service                                                 Network card
216 Receive Requested Application First stage object with DLL references             Network card
                                                                                     Network card
217 Receive Requested Application Data
218
219 Execute Application Second stage compile/interpretation to derive object and referenced DLL*
                                                                                     Primary memory and Secondary memory via DLLs*
220 Execute  Derivative code                                                         Primary memory via chip code
221 Execute  Data access                                                             Primary memory and Secondary memory via DLLs*
222 Develop  Screen images with data content                                         Primary memory and Secondary memory via DLLs*
223 Translate Screen images   example HTML, XML etc.                                 Primary memory and Secondary memory via DLLs*
224 Display    Screen images                                                         Video card
225 Collect    keystrokes/mouse clicks                                               Interface card
226 Transmit   keystrokes/mouse clicks                                               Network card
227 Store      keystrokes/mouse clicks                                               Interface card, Primary memory
228 Analyze    keystrokes/mouse clicks                                               Primary memory via DLLs*

FIG. 5.

Client Server
New Application programming
using a Public Network - Internet

Server CPU activities

| | | | |
|---|---|---|---|
| 101 | Store | DLL Objects | Secondary memory via DLLs |
| 102 | Store | Full and complex Operating System | Secondary memory via DLLs |
| 103 | Store | Application Source Program | Secondary memory via DLLs |
| 104 | Store | Application Data Access programs | Secondary memory via DLLs |
| 105 | Store | Network programs | Secondary memory via DLLs |
| 106 | | | |
| 107 | Store | Browser program ex. Internet Explorer or Netscape | Secondary memory via DLLs |
| 108 | Store | Internet Protocols | Secondary memory via DLLs |
| 109 | Store | Application Data | Secondary memory via DLLs |
| 110 | Store | Application First stage object with DLL references | Secondary memory via DLLs |
| 111 | Execute | Operating System   example  Microsoft | Primary memory and Secondary memory via DLLs |
| 112 | | | |
| 113 | Execute | Network program Internet protocols | Network card |
| 114 | Receive | Request from Client | Network card |
| 115 | Analyze | Request | Primary memory via DLLs |
| 116 | Select | Requested Application First stage compile object and linked DLL object references | Primary memory via DLLs |
| | | | Primary memory and Secondary memory, via DLLs |
| 117 | Select | Requested Data | Primary memory and Secondary memory, via DLLs |
| 118 | | | |
| 119 | | | |
| 120 | Execute | Application Second stage compile/interpretation to derive object and referenced DLL | Primary memory and Secondary memory via DLLs |
| 121 | Execute | Derivative code | Primary memory via chip code |
| 122 | Execute | Data access | Primary memory and Secondary memory via DLLs |
| 123 | Develop | Screen images with requested data content | Primary memory and Secondary memory via DLLs |
| 124 | Translate | Screen images to Public protocol, example HTML, XML, etc. | Primary memory and Secondary memory via DLLs |
| 125 | Transmit | Translated screen images | Network card |
| 126 | Store | keystrokes/mouse clicks | Interface card and Primary memory |
| 127 | Receive | keystrokes/mouse clicks | Network card and Primary memory |
| 128 | Analyze | keystrokes/mouse clicks | Primary memory via DLLs |

*FIG. 6.*

Client Server
New Application programming
using a Public Network - Internet

Client CPU  activities

201 Store  DLL* Objects                                                     Secondary memory via DLLs*
202
203 Store  Minimal Operating System                                         Secondary memory or PROM chip
204
205 Store  Browser program ex. Internet Explorer or Netscape                Secondary memory or PROM chip
206
207
208 Store  Internet Protocols                                               Secondary memory via DLLs*
209
210
211
212 Execute Minimal Operating System                                        Primary memory via DLLs* or PROM chip
213
214 Execute Browser using internet protocols                                Network card
215 Send Request for program service                                        Network card
216
217
218 Receive Requested translated screen images with requested data content
219                                                                         Network card
220
221
222
223
224 Display    Screen images                                                Video card
225 Collect    keystrokes/mouse clicks                                      Interface card
226 Transmit   keystrokes/mouse clicks                                      Network card
227 Store      keystrokes/mouse clicks                                      Interface card, Primary memory
228 Analyze    keystrokes/mouse clicks                                      Primary memory via DLLs*

FIG. 7.

Client Server programming
All activities

Server CPU

| | | | |
|---|---|---|---|
| 101 | Store | DLL Objects | Secondary memory via DLLs |
| 102 | Store | Full and complex Operating System | Secondary memory via DLLs |
| 103 | Store | Application Source Program | Secondary memory via DLLs |
| 104 | Store | Application Data Access programs | Secondary memory via DLLs |
| 105 | Store | Network programs | Secondary memory via DLLs |
| 106 | Store | Private Network Protocols | Secondary memory via DLLs |
| 107 | Store | Browser program ex. Internet Explorer or Netscape | Secondary memory via DLLs |
| 108 | Store | Internet Protocols | Secondary memory via DLLs |
| 109 | Store | Application Data | Secondary memory via DLLs |
| 110 | Store | Application First stage object with DLL references | Secondary memory via DLLs |
| 111 | Execute | Operating System  example  Microsoft | Primary memory and Secondary memory via DLLs |
| 112 | Execute | Network program using Private network protocols | Network card |
| 113 | Execute | Network program Internet protocols | Network card |
| 114 | Receive | Request from Client | Network card |
| 115 | Analyze | Request | Primary memory via DLLs |
| 116 | Select | Requested Application First stage compile object and linked DLL object references | Primary memory and Secondary memory, via DLLs |
| 117 | Select | Requested Data | Primary memory and Secondary memory, via DLLs |
| 118 | Transmit | Requested Application First stage object with DLL references | Network card |
| 119 | Transmit | Requested Application Data | Network card |
| 120 | Execute | Application Second stage compile/interpretation to derive object and referenced DLL | Primary memory and Secondary memory via DLLs |
| 121 | Execute | Derivative code | Primary memory via chip code |
| 122 | Execute | Data access | Primary memory and Secondary memory via DLLs |
| 123 | Develop | Screen images with requested data content | Primary memory and Secondary memory via DLLs |
| 124 | Translate | Screen images to Public protocol, example HTML, XML, etc. | Primary memory and Secondary memory via DLLs |
| 125 | Transmit | Translated screen images | Network card |
| 126 | Store | keystrokes/mouse clicks | Interface card and Primary memory |
| 127 | Receive | keystrokes/mouse clicks | Network card and Primary memory |
| 128 | Analyze | keystrokes/mouse clicks | Primary memory via DLLs |

FIG. 8.

Client Server programming
All activities

Client CPU

| | | | |
|---|---|---|---|
| 201 | Store | DLL* Objects | Secondary memory via DLLs* |
| 202 | Store | Full and complex Operating System | Secondary memory via DLLs* |
| 203 | Store | Minimal Operating System | Secondary memory or PROM chip |
| 204 | Store | Application Data Access programs | Secondary memory via DLLs* |
| 205 | Store | Browser program ex. Internet Explorer or Netscape | Secondary memory or PROM chip |
| 206 | Store | Network program | Secondary memory via DLLs* |
| 207 | Store | Private Network Protocols | Secondary memory via DLLs* |
| 208 | Store | Internet Protocols | Secondary memory via DLLs* |
| 209 | Store | Requested Application Data set | Secondary memory via DLLs* |
| 210 | Store | Application First stage object with DLL references | Secondary memory via DLLs* |
| 211 | Execute | Operating System  example Microsoft | Primary memory and Secondary memory via DLLs* |
| 212 | Execute | Minimal Operating System | Primary memory via DLLs* or PROM chip |
| 213 | Execute | Network program using private network protocols | Network card |
| 214 | Execute | Browser using internet protocols | Network card |
| 215 | Send | Request for program service | Network card |
| 216 | Receive | Requested Application First stage object with DLL references | Network card |
| 217 | Receive | Requested Application Data | Network card |
| 218 | Receive | Requested translated screen images with requested data content | Network card |
| 219 | Execute | Application Second stage compile/interpretation to derive object and referenced DLL* | Primary memory and Secondary memory via DLLs* |
| 220 | Execute | Derivative code | Primary memory via chip code |
| 221 | Execute | Data access | Primary memory and Secondary memory via DLLs* |
| 222 | Develop | Screen images with data content | Primary memory and Secondary memory via DLLs* |
| 223 | Translate | Screen images  example HTML, XML etc. | Primary memory and Secondary memory via DLLs* |
| 224 | Display | Screen images | Video card |
| 225 | Collect | keystrokes/mouse clicks | Interface card |
| 226 | Transmit | keystrokes/mouse clicks | Network card |
| 227 | Store | keystrokes/mouse clicks | Interface card, Primary memory |
| 228 | Analyze | keystrokes/mouse clicks | Primary memory via DLLs* |

*Potential DLL differences between each computer also referenced as Binary incompatibilities

FIG. 9.
(PRIOR ART)

Client Server
Old Application Model
Private Network

Server Computer Example Activity order

Pre Session activities

| Step | Activity number | | Activity description | |
|---|---|---|---|---|
| 1. | 101 | Store | DLL Objects | Secondary memory via DLLs |
| 2. | 102 | Store | Full and complex Operating System | Secondary memory via DLLs |
| 3. | 103 | Store | Application Source Program | Secondary memory via DLLs |
| 4. | 104 | Store | Application Data Access programs | Secondary memory via DLLs |
| 5. | 105 | Store | Network programs | Secondary memory via DLLs |
| 6. | 106 | Store | Private Network Protocols | Secondary memory via DLLs |
| 7. | 109 | Store | Application Data | Secondary memory via DLLs |
| 8. | 110 | Store | Application First stage object with DLL references | Secondary memory via DLLs |
| 9. | 111 | Execute | Operating System example Microsoft | Primary memory and Secondary memory via DLLs |

Begin repeatable cycle within each session:

| | | | | |
|---|---|---|---|---|
| 10. | 112 | Execute | Network program using Private network protocols | Network card |
| 11. | 114 | Receive | Request from Client | Network card |
| 12. | 127 | Receive | keystrokes/mouse clicks | Network card and Primary memory |
| 13. | 126 | Store | keystrokes/mouse clicks | Interface card and Primary memory |
| 14. | 128 | Analyze | keystrokes/mouse clicks | Primary memory via DLLs |
| 15. | 115 | Analyze | Request | Primary memory via DLLs |
| 16. | 116 | Select | Requested Application First stage compile object and linked DLL object references | Primary memory and Secondary memory, via DLLs |
| 17. | 117 | Select | Requested Data | Primary memory and Secondary memory, via DLLs |
| 18. | 112 | Execute | Network program using Private network protocols | Network card |
| 19. | 118 | Transmit | Requested Application First stage object with DLL references | Network card |
| 20. | 119 | Transmit | Requested Application Data | Network card |

Go back to step 10

FIG. 10a.
(PRIOR ART)

Client Server
Old Application Model
Private Network

Client Computer  Example Activity order

Pre Session activities
Step  Activity number  Activity description
1   201 Store    DLL*, Objects                                                    Secondary memory via DLLs*
2   202 Store    Full and complex Operating System                                Secondary memory via DLLs*
3   204 Store    Application Data Access programs                                 Secondary memory via DLLs
4   206 Store    Network program                                                  Secondary memory via DLLs*
5   207 Store    Private Network Protocols                                        Secondary memory via DLLs*
6   211 Execute  Operating System  example Microsoft                              Primary memory and Secondary memory via DLLs*
7   225 Collect  keystrokes/mouse clicks                                          Interface card
8   227 Store    keystrokes/mouse clicks                                          Interface card, Primary memory
9   228 Analyze  keystrokes/mouse clicks                                          Primary memory via DLLs*

Begin repeatable major cycle within each session:

10  213 Execute  Network program using private network protocols                  Network card
11  215 Send     Request for program service                                      Network card
12  226 Transmit keystrokes/mouse clicks                                          Network card
13  213 Execute  Network program using private network protocols                  Network card
14  216 Receive  Requested Application First stage object with DLL references     Network card
15  210 Store    Application First stage object with DLL references               Secondary memory via DLLs*
16  217 Receive  Requested Application Data                                       Network card
17  209 Store    Requested Application Data set                                   Secondary memory via DLLs*
18  219 Execute  Application Second stage compile/interpretation to derive object and referenced DLL*
                                                                                  Primary memory and Secondary memory via DLLs*
19  220 Execute  Derivative code                                                  Primary memory via chip code
20  221 Execute  Data access                                                      Primary memory and Secondary memory via DLLs*
21  222 Develop  Screen images with data content                                  Primary memory and Secondary memory via DLLs*
22  223 Translate Screen images  example HTML, XML etc.                           Primary memory and Secondary memory via DLLs*
23  224 Display  Screen images                                                    Video card
24  225 Collect  keystrokes/mouse clicks                                          Interface card
25  227 Store    keystrokes/mouse clicks                                          Interface card, Primary memory
26  228 Analyze  keystrokes/mouse clicks                                          Primary memory via DLLs*

*FIG. 10b.*
*(PRIOR ART)*

Client Server
Old Application.Model
Private Network
Client Computer   Example Activity order
Continued:

Either go to step 10
Or continue to step 27
Or discontinue session

Repeatable cycle within the major cycle

| | | | |
|---|---|---|---|
| 27 | | | |
| | 219 | Execute  Application Second stage compile/interpretation to derive object and referenced DLL* | |
| 28 | 220 | Execute  Derivative code | Primary memory and Secondary memory via DLLs* |
| 29 | 221 | Execute  Data access | Primary memory via chip code |
| 30 | 222 | Develop Screen images with  data content | Primary memory and Secondary memory via DLLs* |
| 31 | 223 | Translate Screen images    example HTML, XML etc. | Primary memory and Secondary memory via DLLs* |
| 32 | 224 | Display     Screen images | Primary memory and Secondary memory via DLLs* |
| 33 | 225 | Collect     keystrokes/mouse clicks | Video card |
| 34 | 227 | Store       keystrokes/mouse clicks | Interface card |
| | | | Interface card, Primary memory |

Go to step 26

*FIG. 11.*

Client Server
New Application Model
Public Network using the Internet

Server Computer Activity order

Pre session activities
| Step | Activity number | | Activity description | | |
|---|---|---|---|---|---|
| 1 | 101 | Store | DLL Objects | | Secondary memory via DLLs |
| 2 | 102 | Store | Full and complex Operating System | | Secondary memory via DLLs |
| 3 | 103 | Store | Application Source Program | | Secondary memory via DLLs |
| 4 | 104 | Store | Application Data Access programs | | Secondary memory via DLLs |
| 5 | 105 | Store | Network programs | | Secondary memory via DLLs |
| 6 | 107 | Store | Browser program ex. Internet Explorer or Netscape | | Secondary memory via DLLs |
| 7 | 108 | Store | Internet Protocols | | Secondary memory via DLLs |
| 8 | 109 | Store | Application Data | | Secondary memory via DLLs |
| 9 | 110 | Store | Application First stage object with DLL references | | Secondary memory via DLLs |
| 10 | 111 | Execute | Operating System   example  Microsoft | | Primary memory and Secondary memory via DLLs |

Begin repeatable cycle within each session:

| | | | | | |
|---|---|---|---|---|---|
| 11 | 113 | Execute | Network program Internet protocols | | Network card |
| 12 | 114 | Receive | Request from Client | | Network card |
| 13 | 127 | Receive | keystrokes/mouse clicks | | Network card and Primary memory |
| 14 | 126 | Store | keystrokes/mouse clicks | | Interface card and Primary memory |
| 15 | 128 | Analyze | keystrokes/mouse clicks | | Primary memory via DLLs |
| 16 | 115 | Analyze | Request | | Primary memory via DLLs |
| 17 | 116 | Select | Requested Application First stage compile object and linked DLL object references | | Primary memory and Secondary memory, via DLLs |
| 18 | 117 | Select | Requested Data | | Primary memory and Secondary memory, via DLLs |
| 19 | 120 | Execute | Application Second stage compile/interpretation to derive object and referenced DLL | | Primary memory and Secondary memory via DLLs |
| 20 | 121 | Execute | Derivative code | | Primary memory via chip code |
| 21 | 123 | Develop | Screen images with requested data content | | Primary memory and Secondary memory via DLLs |
| 22 | 124 | Translate | Screen images to Public protocol, example HTML, XML, etc. | | Primary memory and Secondary memory via DLLs |
| 23 | 113 | Execute | Network program Internet protocols | | Network card |
| 24 | 125 | Transmit | Translated screen images | | Network card |

Go back to step 11

FIG. 12.

Client Server
New Application Model
Public Network using the Internet

Client Computer Activity order

Pre Session activities
| Step | Activity number | Activity | description | |
|---|---|---|---|---|
| 1 | 201 | Store | DLL* Objects | Secondary memory via DLLs* |
| 2 | 203 | Store | Minimal Operating System | Secondary memory or PROM chip |
| 3 | 205 | Store | Browser program ex. Internet Explorer or Netscape | Secondary memory or PROM chip |
| 4 | 208 | Store | Internet Protocols | Secondary memory via DLLs* |
| 5 | 212 | Execute | Minimal Operating System | Primary memory via DLLs* or PROM chip |
| 6 | 225 | Collect | keystrokes/mouse clicks | Interface card |
| 7 | 227 | Store | keystrokes/mouse clicks | Interface card, Primary memory |
| 8 | 228 | Analyze | keystrokes/mouse clicks | Primary memory via DLLs* |

Either go to step 9
Or discontinue session

Begin repeatable cycle within each session:
| 9 | 214 | Execute | Browser using internet protocols | Network card |
|---|---|---|---|---|
| 10 | 215 | Send | Request for program service | Network card |
| 11 | 226 | Transmit | keystrokes/mouse clicks | Network card |
| 12 | 214 | Execute | Browser using internet protocols | Network card |
| 13 | 218 | Receive | Requested translated screen images with requested data content | Network card |
| 14 | 224 | Display | Screen images | Video card |
| 15 | 225 | Collect | keystrokes/mouse clicks | Interface card |
| 16 | 227 | Store | keystrokes/mouse clicks | Interface card, Primary memory |

Go to step 8

WEB-SITE HOST CONSISTENCY ADMINISTRATION AMONG INCONSISTENT SOFTWARE-OBJECT LIBRARIES OF REMOTE DISTRIBUTED HEALTH-CARE PROVIDERS

CROSS-REFERENCE TO RELATED APPLICATION(S)

This application is continuation of U.S. patent application Ser. No. 09/761,362, filed Jan. 16, 2001, U.S. Pat. No. 6,751,651, which claims the benefit of U.S. Provisional Application No. 60/176,207, filed Jan. 14, 2000.

This application is related to co-pending, commonly-owned and commonly-invented U.S. patent application Ser. No. 09/726,946, filed Nov. 29, 2000, which claims the benefit of U.S. Provisional Application No. 60/168,114, filed Nov. 30, 1999, and which is incorporated fully herein by this reference to it.

BACKGROUND OF THE INVENTION

The invention generally relates to distributed computer systems and/or networks of interconnected computer systems, and more particularly to a method and system of Web-site host consistency administration among inconsistent software-object libraries of remote distributed health-care providers.

Looked at differently, the problem addressed by the invention relates to person-to-machine interaction with data. By way of background, a Web-site host is entrusted to provide administration services over a client's data. The client—a very real person—receives access to the data in the form of requests transmitted to the host over the Internet. The invention deals with the consistent presentation of requested data on the client's machine. That way, the client (ie., the person) is less likely to mis-interpret the data if it is presented consistently the same time after time.

Preferably the invention is implemented over the Internet to take advantage of its far reach as an affordable communications medium to remote distributed machines. More preferably still is that the given communications transmitted between the Web-site host and its clients over the Internet use open or public domain protocols for doing so. These principally include to date for Web-page matter the languages or formats of HTML (hypertext markup language), SGML (standard generalized markup language), XML (extensible markup language), XSL (extensible style language), or CSS (cascading style sheets).

The present application claims relation to the above-referenced co-pending, commonly-owned and commonly-invented U.S. patent application Ser. No. 09/726,946, filed Nov. 29, 2000, entitled "Process for Administrating over Changes to Server-Administrated Client Records in a Stateless Protocol." The emphasis in that application is on administrating over the trustworthiness of the data. In contrast, the emphasis of the present application is on administrating over the trustworthiness in the presentation.

That is, in the present application the trustworthiness of the data is taken as a given. The problem is, however, even if the data is trustworthy, inconsistent presentation among different requests for the data can cause human error in interpretation of the data.

The matter of consistent presentation of data is critical in field of remote distributed healthcare providers because of the following factors. Medication decisions are based on the data. The data in such case may be the time of previous administration of medication to a patient. If this bit of information fails to land in the right place for it on the client's computer screen, the client might miss it. The client might also not search the screen for where the data is displayed, or not understand it if indeed seen since it's not inside its field. Hence the client might decide to administer the patient a next dose when it's too soon. That's one aspect of the problem.

At this stage, further background into the problem would provide a richer understanding of it. The clients of applicant's enterprise comprise a group of healthcare providers such as nurses (of several types), physicians, social workers, therapists (of several types), or dieticians. The profile of such persons in that group is that they are attending to patients or residents in locations other than big medical complexes like hospitals or the like. Example such "other" locations include home health care provided to a patient in his or her own home, long term care provided to residents of long-term care facilities (eg., nursing homes), or physician offices in rural areas or where otherwise remote from services of Information Technologists. These parties have sophisticated information processing needs. However, they may have no more access to a computer than a personal or laptop computer that can be hooked up to the Internet by a phone line. These parties sorely lack local personal service from a skilled Information Technician because IT's are in short supply about everywhere. These parties troubles will have to be solved on the server-side of operations.

As well understood by those skilled in the art, computers communicating over the World Wide Web ("Web") do so by browser technology and in an environment described as a "stateless" or non-persistent protocol. "Intranet" generally refers to private networks that likewise implement browser technology. "Internet" generally includes the Web as well as sites operating not on browser-technology but perhaps maybe servers of mail or Internet chat and the like. At least in the case of the Web, the stateless protocol is denominated as Hypertext Transfer Protocol ("HTTP").

One premise of the Web is that material on the Web may be formatted in open or "public domain" formats. Several have been named previously. Many if not most of these open formats are produced under the authority of W3C, which is short for World Wide Web Consortium, founded in 1994 as an international consortium of companies involved with the Internet and the Web. The organization's purpose is to develop open standards so that the Web evolves in a single direction rather than being splintered among competing factions. The W3C is the chief standards body for HTTP and HTML and so on.

On the Web, all information requests and responses presumptively conform to one of those standard protocols. Another premise of the Web is that communications vis-a-vis requests and responses are non-persistent. A request comprises a discrete communication which when completed over a given channel is broken. The response thereto originates as a wholly separate discrete communication which is likely to find its way to the requestor by a very different channel.

Additional aspects and objects of the invention will be apparent in connection with the discussion further below of preferred embodiments and examples.

SUMMARY OF THE INVENTION

It is an object of the invention to provide a model method of Web-site host consistency administration among inconsistent software-object libraries of remote distributed health-care providers.

These and other aspects and objects are provided according to the invention in a method and system of Web-site host consistency administration for network communications between a server and remote distributed clients belonging to the health-care provider field and in a computing environment in which the clients are treated as communicating from machines stored with inconsistent software-object libraries.

Aspects of the method comprise the following.

A Web-site host is provided with a rich library of DLL objects, a full and complex operating system, an application source program, application data access program, network program, Internet protocols, application data, and application first-stage-compiled objects with DLL references.

The Web-site host is executing the operating system and further executing a repeatable cycle, which from a beginning comprises these steps.

The host executes the network program using the Internet protocols.

It receives a request from a client in the form of keystrokes and cursor-moving device inputs.

It stores the received keystrokes and cursor-moving device inputs.

The host analyzes the keystrokes and cursor-moving device inputs and in consequence thereof, analyzing the request gotten thereby.

It selects, in accordance with the request, an applicable first-stage-compiled object with linked DLL references.

It selects requested data.

It executes a second-stage-compile/interpretation of the selected first-stage-compiled object with linked DLL references in order to derive object and referenced DLL's.

It executes the derivative code.

The host also develops screen images with requested data content.

It translates the developed screen images into an open or public domain protocol.

It executes the network program using Internet protocols.

The host transmits the translated screen images.

And then, the host goes back to the beginning of the repeatable cycle.

This method thereby provides high assurance that every client sees substantially the same result for the same request despite inconsistencies in DLL libraries onboard different client machines.

Preferably the open protocols comprise one of HTML (hypertext markup language), SGML (standard generalized markup language), XML (extensible markup language), XSL (extensible style language), or CSS (cascading style sheets).

The method may further comprise the following.

That is, a client is provide with a library of DLL objects (but these are presumed inconsistent with those of the server's library), at least a minimal operating system, a browser program, and Internet protocols.

The client executes the at least minimal operating system and further collects and stores keystrokes and cursor-moving device inputs.

The client analyzes the keystrokes and cursor-moving device inputs and either discontinues or else continues by further executing a repeatable cycle, which from a beginning comprises the following steps.

The client executes the browser program using the Internet protocols.

The client sends a request for Web-site host service in the form of the stored keystrokes and cursor-moving device inputs.

The client executes the browser program using the Internet protocols.

The client receives the requested translated screen images with requested data content.

The client displays the screen images.

The client collects and stores keystrokes and cursor-moving device inputs.

And then the client goes back to the step of analyzing the keystrokes and cursor-moving device inputs at the beginning of the repeatable cycle. Again this further development of the method on the client-side of processing further provides high assurance a common look for every request despite inconsistencies in DLL libraries onboard different client machines.

In this method, the remote distributed clients belonging to the health-care provider field preferably include nurses of varying types, physicians, social workers, therapists of several types, or dieticians providing service to a patient at home, a resident of a nursing home, or a patient at a physician's office remote from a medical complex.

Additional aspects and objects of the invention will be apparent in connection with the discussion further below of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 3 is a table of prior art server-side CPU activities for a server practicing the prior art client/server model for network communications of FIG. 1;

FIG. 4 is a table of prior art client-side CPU activities for a client participating in the prior art client/server model for network communications of FIG. 1;

FIG. 5 is a table comparable to FIG. 3 except showing server-side CPU activities for a server practicing the Web-site host consistency administration model in accordance with the invention for network communications (eg., FIG. 2);

FIG. 6 is a table comparable to FIG. 4 except showing client-side CPU activities for a client participating in the Web-site host consistency administration model in accordance with the invention for network communications (eg., FIG. 2);

FIG. 7 is a table comparable to both FIGS. 3 and 5 or more accurately, combining FIGS. 3 and 5 to show together in one table all server-side CPU activities presented in either FIG.

Figure 1:
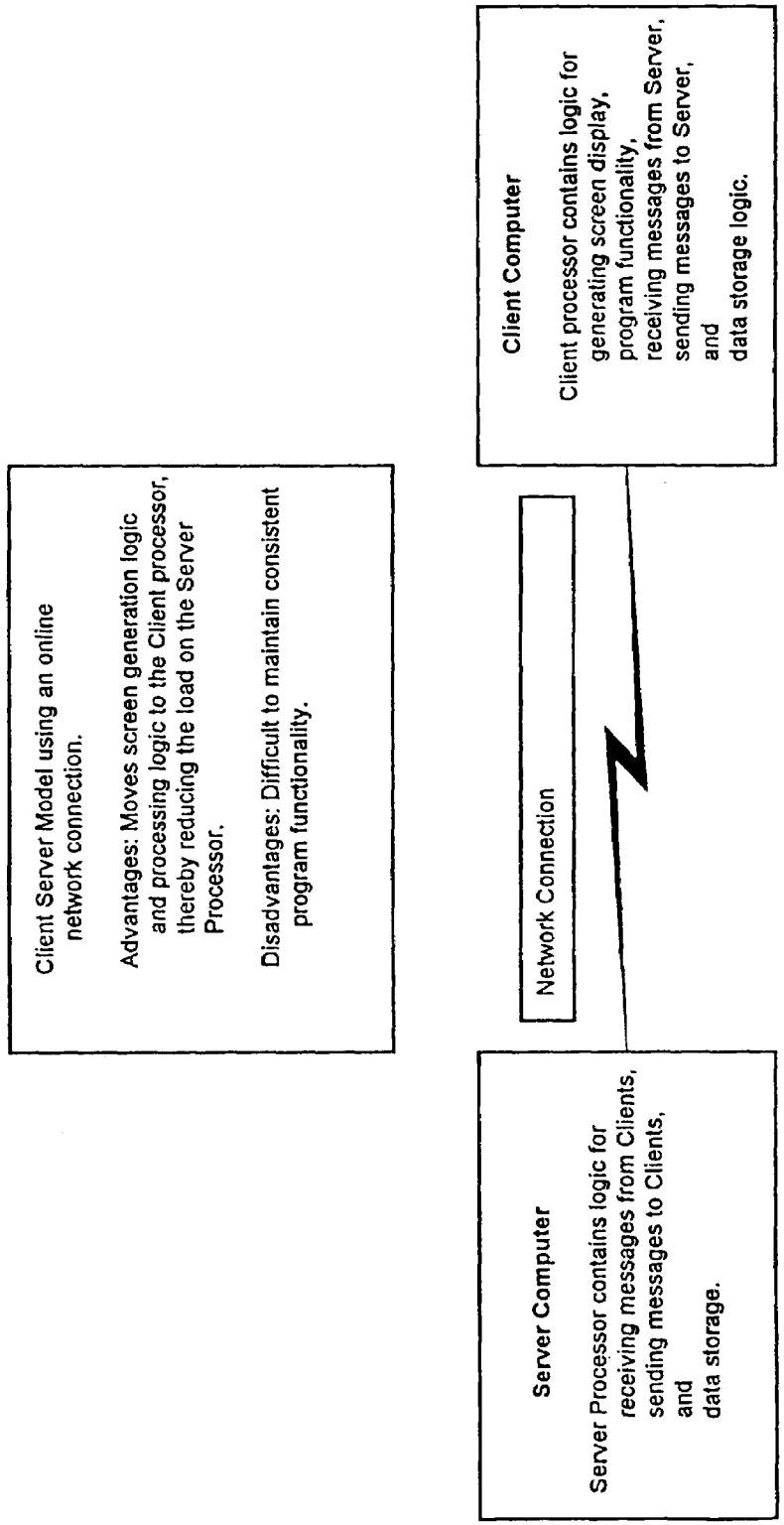
FIG. 1 is a block diagrammatic view of a prior art client/server model for network communications between a server and clients (one client shown)
Figure 2:
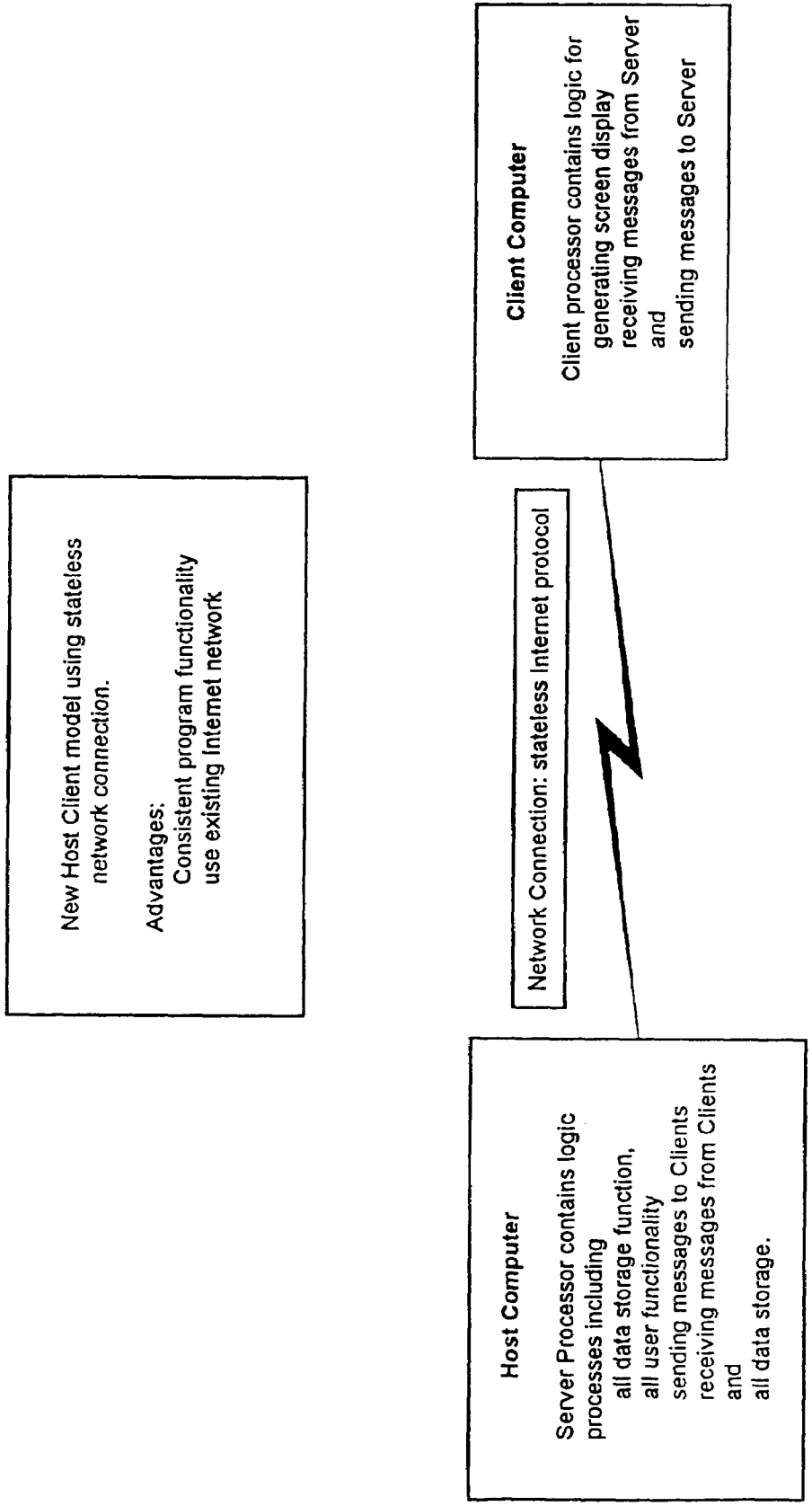
FIG. 2 is a block diagrammatic view of a Web-site host consistency administration model in accordance with the invention for network communications between a server and remote distributed clients (one shown) belonging to the health-care provider field and in a computing environment in which the clients are treated as communicating from machines loaded with inconsistent software-object libraries.
Figures 10, 10A, 10B:
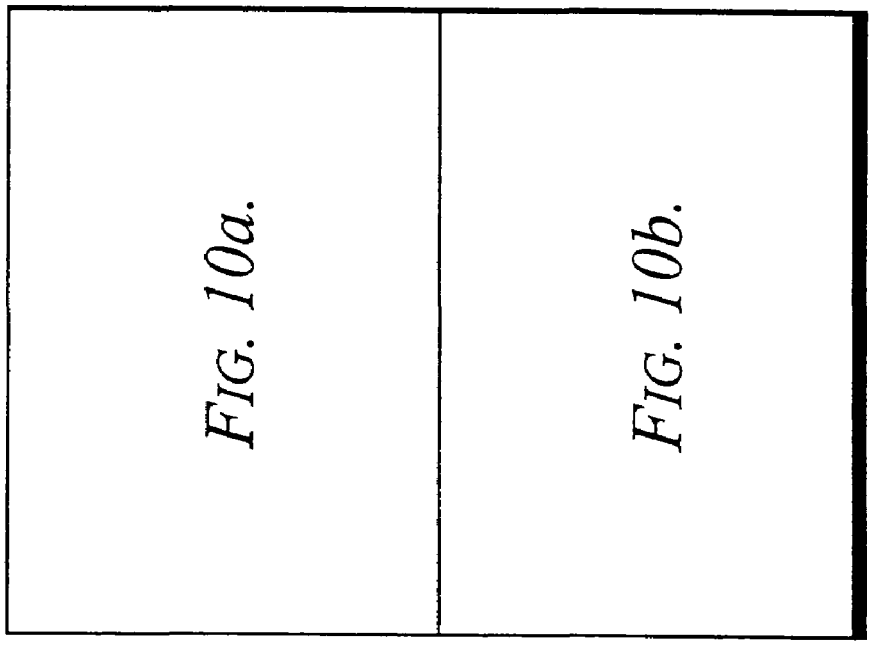

3 for the prior art client/server model or else in FIG. 5 for the Web-site host consistency administration model in accordance with the invention;

FIG. 8 is a table comparable to both FIGS. 4 and 6 or more accurately, combining FIGS. 4 and 6 to show together in one table all client-side CPU activities presented in either FIG. 4 for the prior art client/server model or else in FIG. 6 for the Web-site host consistency administration model in accordance with the invention;

FIG. 9 is a table-form flowchart of process sequence and logic for the server practicing the prior art client/server model for network communications of FIG. 1;

FIG. 10 shows that FIGS. 10a and 10b combine as depicted since the content of FIG. 10a continues over onto FIG. 10b, wherein FIGS. 10a and 10b in combination provide a table-form flowchart of process sequence and logic for the client participating in the prior art client/server model for network communications of FIG. 1;

FIG. 11 is a table-form flowchart comparable to FIG. 9 except showing process sequence and logic for a server practicing the Web-site host consistency administration model in accordance with the invention for network communications (eg., FIG. 2); and, FIG. 12 is a table-form flowchart comparable to FIGS. 10a and 10b except showing process sequence and logic for a client participating in the Web-site host consistency administration model in accordance with the invention for network communications (eg., FIG. 2).

DETAILED DESCRIPTION OF THE PREFERRED EMBODIMENTS

FIG. 2, then 4–6 and after that 11–12 illustrate a Web-site host consistency administration method in accordance with the invention for remote distributed health-care providers whose machines are presumed to store inconsistent software-object libraries.

Arguably, the best understanding of the invention is gotten by comparing FIG. 12 to the prior art shown by FIGS. 10a and 10b, or else FIG. 11 to the prior art shown by FIG. 9. The views of FIGS. 1 through 8 might be best appreciated as providing support to an ultimate understanding of the matters presented in the latter views of FIGS. 9–12.

The invention applies to network communications between a Web-site host and remote distributed clients. FIG. 12 shows CPU process sequence and logic for a client participating in the Web-site host consistency administration method in accordance with the invention (eg., FIG. 2). For comparison, FIGS. 10a and 10b show client-side CPU process sequence and logic for the prior art client/server model of operations.

FIG. 11 shows CPU process sequence and logic for the host practicing the Web-site host consistency administration method in accordance with the invention (eg., FIG. 2). For comparison, FIG. 9 shows server-side CPU process sequence and logic for the prior art client/server model of operations.

As a brief background in terminology, the term "server" or "host" is used fairly consistently as short for server domain. A server domain may comprise one or more server machines cooperating as a unitary server domain. The database and engines might be supplied to the server through a vendor such as ORACLE® or the like. The term "client" is most often used in context as an individual person who identifies him or herself with the server through an account.

FIG. 1 is a block diagrammatic view of a prior art client/server model for network communications between a server and a client. It is assumed that this model operates by means of an online, real-time, persistent protocol.

The advantages of this prior art model include taking advantage of distributed computing on a large even global scale. This involves a network of user machines (PC's or laptops?) connected via moderate bandwidth, low-latency networks which as a whole cooperate as a computing platform. The goal has been to take advantage of a large resource pool of PC's comprising hundreds of gigabytes of memory, terabytes of disk space, and hundreds of gigaflops of processing power that is often idle. This paradigm in computing was expected to impact the fundamental design techniques for large systems and their ability to solve large problems, service a large number of users, and provide a computing infrastructure. Hence substantial amounts of screen generation logic as well processing and data manipulation logic is moved onto the user machines. This reduced the load on the server processor by distributing the processing load among the users.

However, there are several disadvantages of this FIG. 1 model of operations. It is difficult to maintain consistent program functionality. The clients are likely to inconsistent software-object libraries and it is these inconsistencies which make it difficult to maintain consistent program functionality.

These software-object libraries store the Dynamic Link Library objects (eg., DLLs). On a Microsoft® operating system, these objects take the *.dll extension. DLLs provide a call to oft-used functionality. Microsoft provides standardized packages of DLLs in order to provide a consistent computing platform between machines transferring communications over a network. Revealing evidence has surfaced that DLLs are problematical, leading to incompatibilities. They fail to provide a homogeneous family of computing platforms.

Consider the Windows 95® operating system product. It is supposed to provide a homogeneous family of DLLs such that networked computers provide a homogeneous family of computing platforms. However, applicant is aware that the Windows 95® product was issued from Microsoft® in five different series of DLL packages. The Windows 95® product provide hundreds of DLL objects. But in each different series, the DLL packages differed slightly.

More troubling is that some third-party software providers are modifying Microsoft®'s standard DLLs. For example, say a given DLL is supposed to produce a blue button centered in a yellow box. If a third-party software programmer wants that functionality, then it call that object. What is happening is that some third-party software programmers want to vary that result slightly for their own programs. When that program is loaded onto a machine it overwrites the standard DLL with a modified DLL. Following that, perhaps every call to that DLL will produce a yellow-green box with a non-centered button.

It is believed that game software causes the most corruption of Microsoft®'s standard package of DLLs. Notwithstanding games, applicant provided the following demonstration of the problem. Applicant searched on a given PC operating on Windows 98® (second version) for all files "*.dll" file extension. Of the more than a thousand files, it was apparent that the majority of the files in the "c:/windows/systems" folder were last modified on Apr. 23, 1999, at 10:22 pm. Subsequent to that time, RealPlayer® was downloaded off the Internet at say Jan. 29, 2000, and 1:35 pm. That action seems to have produced a download of eighty new *.dll files. Significantly, that action seems to have produced the overwrite of four (4) original *.dll files in the "c:/windows/systems" folder. Over time, with successive loading of more software onto the operating system, this problem creeps up until such a significant portion of the standard DLL package has been corrupted that its functionality can be no longer assured.

To turn to the invention, FIG. 2 provides a block diagrammatic view of a Web-site host consistency administration model in accordance with the invention. The invention provides for network communications between a server and remote distributed clients (one shown) belonging to the health-care provider field and in a computing environment in which the clients are treated as communicating from machines loaded with inconsistent software-object libraries.

This field of clients classifies, more particularly, into the fields of Long Term Care (LTC), Home Health Care (HHC), and Physicians offices (PO). The following are some of the problems that exist currently. The majority of the LTCs are geographically dispersed, independent, and need no more than 5 to 10 users or computer nodes. But each has very sophisticated data needs. Program updates are needed frequently. The facilities do not have sophisticated computer support, and if it is available locally, and is likely too expensive. PC's are available locally, but the additional PCs purchased at different times, will not have the same operating system versions so installed user programs will not always work the same. This is the DLL problem referenced above. Microsoft® calls the problem Binary incompatibilities. Data storage and backups are a problem at the local level. If the facility is part of a group, installing a dedicated line to each facility is expensive.

The HHC industry's services are delivered by traveling nursing personnel. They go to each home and give care. They need a computer for record keeping and to support centralized billing at the agency office. The offices can be computer savvy but they have to be connected to the caregiver. Establishing a dedicated line to each customer is not possible. But almost every home has a phone line and then also a cell phone attached to a notebook computer and access the Internet is possible and will be common. The Internet is a perfect solution. The data needs for this area are very sophisticated and similar to the LTC industry.

POs that are geographically disbursed from the hospitals or else independent physicians need access to very sophisticated computer programs and data storage.

All of the above three groups have similar problems. They need sophisticated programs, data storage, patient/resident records, billing records, accounting, scheduling and so on. At the point of use, these groups likely have no adequate local information technology expertise available for help. Also, these groups are likely are wanting to use just cheap off-the-shelf PCs. Nevertheless all have access to phone lines or cell phones.

The invention provides the following advantages. Since the Internet is everywhere, sharing communication/phone lines so keeps the cost of the communications medium comparatively low. There is no need for local staff to write, maintain, modify programs, or to monitor data storage and backups. The Web-site host/service provider with a staff over the Internet provides these services.

To deal with PC's bought at different times having different operating systems causing loaded programs to not operate the same, the invention download HTML or XML code or the like on demand in real time, using only the low level and small browser within the operating system. As programs change, it is hard to load all the HHC PCs with the correct programs. Hence there is maintained only one copy of the most current programs at the service provider which downloads HTML or XML and or the like on demand in real time via phone line or cell phone attached to portable notebook computer. There is no retention of data on the client machines. If an HHC has to upload all of days or weeks activity and get schedules this is a big hassle and if lost the whole week is lost. If all the data is at the service provider the local PC has no data to upload or schedule to download.

The invention provides the following benefits. There is low cost in the communication connection. Communication is available from everywhere. Using HTML or XML code or the like that is downloaded on demand in real-time interactively via a browser solves the Binary incompatibility problem and makes any off-the-shelf PC a potential user machine. The invention allows for centralized program and data storage and solves the data version problem that currently exists in the client server method. Cell phones or satellite communications provide alternative channels to get to the Internet.

FIGS. 3 through 12 show how the problem of binary incompatibilities is solved or minimized. In short, the host communicates in way with the client that is least likely to contact the DLLs onboard the client. On the client, processing is achieved not only in the main CPU but in the network interface cards. The interface cards have DLL objects but as they are coded onto PROM chips they are virtually invulnerable to corruption by third-party software vendors.

FIG. 3 provides a table of prior art server-side CPU activities for a server practicing the prior art client/server model for network communications of FIG. 1. Activity 102 recites that a full and complex operating system gets loaded into secondary memory (eg., hard-drives) by processes that use DLL's. Activity 110 recited that the application program undergoes a first-stage compile process calling to produce a first-stage object with DLL references, which gets stored on secondary memory.

FIG. 4 provides a table of prior art client-side CPU activities for a client participating in the prior art client/server model for network communications of FIG. 1. Activity 219 recites that the requested first-stage object with DLL references undergoes a second-stage compile/interpretation process to derive an object and references to the DLLs* on the client machine. The DLLs* on the client machine are asterisked because there are potential differences between the DLLs on the server and the corresponding DLLs* on the client machine. Activity 220 recites that the client machine executes the derivative code so derived.

FIG. 5 is a table comparable to FIG. 3 except showing server-side CPU activities for a server practicing the Web-site host consistency administration model in accordance with the invention for network communications (eg., FIG. 2). FIG. 6 is a table comparable to FIG. 4 except showing client-side CPU activities for a client participating in the Web-site host consistency administration model in accordance with the invention for network communications (eg., FIG. 2).

Relatively speaking, the host in accordance with the invention is carrying a heavier processing load than the server in the prior art client/server model. Correspondingly, the client in accordance with the invention is carrying a lighter processing load than the client in the prior art client/server model.

FIG. 7 is a table comparable to both FIGS. 3 and 5 or more accurately, combining FIGS. 3 and 5 to show together in one table all server-side CPU activities presented in either FIG. 3 for the prior art client/server model or else in FIG. 5 for the Web-site host consistency administration model in accordance with the invention. Similarly, FIG. 8 is a table comparable to both FIGS. 4 and 6 or more accurately, combining FIGS. 4 and 6 to show together in one table all client-side CPU activities presented in either FIG. 4 for the prior art client/server model or else in FIG. 6 for the Web-site host consistency administration model in accordance with the invention.

FIG. 9 is a table-form flowchart of process sequence and logic for the server practicing the prior art client/server model for network communications of FIG. 1.

FIG. 10 shows that FIGS. 10a and 10b combine as depicted since the content of FIG. 10a continues over onto FIG. 10b. FIGS. 10a and 10b in combination provide a table-form flowchart of process sequence and logic for the client participating in the prior art client/server model for network communications of FIG. 1.

FIG. 11 is a table-form flowchart comparable to FIG. 9 except showing process sequence and logic for a server practicing the Web-site host consistency administration model in accordance with the invention for network communications (eg., FIG. 2). FIG. 12 is a table-form flowchart comparable to FIGS. 10a and 10b except showing process sequence and logic for a client participating in the Web-site host consistency administration model in accordance with the invention for network communications (eg., FIG. 2).

Comparing FIG. 12 to the prior art client of FIGS. 10a and 10b show that the invention contacts many fewer of the DLL objects on the client machines than the prior art method. The critical screen painting activities optimally contact none.

Comparing FIG. 11 to the prior art server of FIG. 9 shows that the host in accordance with the invention is carrying a heavier processing load in relation to the server of the prior art client/server model.

The distinction of the invention and the prior art may be made more clear through the following example.

Assume that a client wants to administer a medication. The client needs to know if mediation was previously administrated according to schedule as well as if any conditions are noted to modify the administration of that medication. For example, should the client check blood sugar level and note the levels to allow administration of medication, or check blood pressure and compare to previous levels and note the levels to allow administration?

In general, the client shall do the following, regardless of the model. That is, the client connects to the host or server site (eg., the data center) and:
  requests the patient's data,
  requests medication administration data,
  requests identified medication schedule and notes,
  performs the noted observation activity,
  enters results of observation, and
  receives the programs analysis.

The client then makes a decision if to administrate the medication. If so, the client records the activity.

If the client is participating in the prior art client/server model of operations, then the client CPU will do the following (ie., FIG. 11), ie, the client CPU will:
  connect to data center,
  accept keystrokes/mouse inputs,
  analyze for forming a request,
  transmit the request to the data center,
  receive the First-stage Object and referenced DLLs,
  receive the requested data,
  execute the Second stage compile/interpretation of the object and referenced DLL's,
  develop the screen and screen content display the developed screen,
accept keystrokes/mouse inputs,
analyze keystrokes/mouse inputs,
develop and display a different screen and screen content,
accept keystrokes/mouse inputs,
analyze keystrokes/mouse inputs, and
either
  build another different screen,
  or Transmit a request to data center for additional Data and First stage objects and DLL references, and so on continuing the process.

All of the above example could be executed with two or three requests to the Server CPU (depends on program design).

As the DLL's in this Client are not the same as the DLLs in the Server; the functionality and display of results on the Client CPU may not be the same. Computations may not be consistent and results may not be displayed in the expected area or with the expected nomenclature. All the above activity takes place within the Client CPU.

If we are using the inventive Web-site host consistency administration model in accordance with the invention (FIG. 12), the Client CPU will do the following:
  connect to data center,
  accept keystrokes/mouse inputs,
  transmit request to data center,
  receive first screen with data,
  display the screen
  accept keystrokes/mouse inputs,
  transmit keystrokes/mouse inputs,
  receive next screen with data,
  display the screen, and so on, in continuation of the process.

The above example could take more than ten (10) requests to the host CPU (depends on program design) to accomplish the same as two or three (2 or 3) requests pursuant to the prior art. As no computation is taking place on this CPU, all computation and screen content and generation is on the host server. The First sage objects with references to DLL and the same as the Second stage interpretation with the DLL of the server. Therefore the screen displays are consistent and the computations are consistent.

So while the invention requires many more transmissions than the prior art model to accomplish comparable functionality, the invention provides a higher assurance that a given request will produce the same results no matter what machine or in what state of corruption the onboard DLLs exist.

That is, the model in accordance with the invention prefers to send more data from host to client than the prior art, and many more times, rather than rely on the DLL package onboard the client's machines.

The client is going to make critical decisions based on the data. Accordingly, its trustworthiness is paramount, including its presentation. This way, the host is more highly assured that each client sees the identical same result for the same request. Or alternatively, a given person is more highly assured of seeing the identical same result for a same request no matter is sent from different machines during different sessions. That way, the presentation of the data is more assured of being consistent from time to time and therefore makes less chance of improper human interpretation.

Accordingly, the invention having been disclosed in connection with the foregoing variations and examples, additional variations will now be apparent to persons skilled in the art. Parts of the description uses terms for a computer network such as server, client, user, browser, machine and the like, consistent with the manner commonly employed by those skilled in the art to convey the substance of their work to others skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A method for excusing clients from most of the processing load in a server-client health care network, comprising the steps of:

providing a Web-site host for consistency administration over network communications between a server and remote distributed clients belonging to the health-care provider field and in a computing environment in which the clients are treated as communicating from machines stored with inconsistent software-object libraries;

limiting a given client's role to displaying received screens, sending out electronic input requests, wherein said Web-site host consistently provides presentation of data derived from selected object and linked DLL and/or additional object references to the given client by analyzing the electronic input requests from the given client;

providing the Web-site host with a library of DLL and/or additional complete or incomplete objects, a sufficient operating system, an application source program, application data access program, network program, Internet protocols, application data, and application first-stage-compiled objects with DLL and/or additional complete or incomplete objects references;

the Web-site host executing the operating system and further executing a repeatable cycle, which from a beginning comprises:

executing the network program using the Internet protocols;

receiving a request from a client in an electronic form;

storing the received request;

analyzing the received request and in consequence thereof, analyzing the request gotten thereby;

selecting, in accordance with the request, an applicable first-stage-compiled complete or incomplete object with or without additional linked DLL and/or additional complete or incomplete object references;

selecting requested data;

executing a second-stage-compile/interpretation of the selected first-stage-compiled complete or incomplete object with additional linked DLL and/or additional complete or incomplete object references in order to derive a new temporary executable object;

executing the derivative code;

developing screen images with requested data content;

translating the developed screen images into an open or public domain protocol;

executing network program Internet protocols;

transmitting the translated screen images; and, going back to the beginning of the repeatable cycle, whereby said method provides high assurance that every client sees substantially the same result for the same request despite inconsistencies in DLL and/or object libraries onboard different client machines.

2. The method of claim 1 wherein the open or public domain protocol comprises one of HTML (hypertext markup language), SGML (standard generalized markup language), XML (extensible markup language), XSL (extensible style language), or CSS (cascading style sheets).

3. The method of claim 1 wherein the remote distributed clients belonging to the health-care provider field include nurses of varying types, physicians, social workers, therapists of several types, or dieticians providing service to a patient at home, a resident of a nursing home, or a patient at a physician's office remote from a medical complex.

4. A method for excusing clients from most of the processing load in a server-client health care network, comprising the steps of:

providing a Web-site host for consistency administration over network communications between a server and remote distributed clients belonging to the health-care provider field and in a computing environment in which the clients are treated as communicating from machines stored with inconsistent software-object libraries;

limiting a given client's role to displaying received screens, sending out electronic input requests, wherein said Web-site host consistently provides presentation of data derived from selected object and linked DLL and/or additional object references to the given client by analyzing the electronic input requests from the given client;

providing the clients with a library of DLL and/or additional complete or incomplete objects which are presumed inconsistent with those of the server's library, at least a minimal operating system, a browser program, and Internet protocols;

the given client executing the at least minimal operating system and further collecting and storing electronic input requests;

analyzing the electronic input requests and either discontinuing or else continuing by further executing a repeatable cycle, which from a beginning comprises:

executing the browser program using the Internet protocols;

sending a request for Web-site host service in the form of a transmission of applicable ones of the stored electronic input requests;

executing the browser program using the Internet protocols;

receiving the requested translated screen images with requested data content;

displaying the screen images;

collecting and storing electronic input requests; and, going back to the step of analyzing the electronic input requests at the beginning of the repeatable cycle, whereby said method on the client-side of processing further provides high assurance a common look for every request despite inconsistencies in DLL and/or object libraries onboard different client machines.

5. The method of claim 4 wherein the clients' libraries of DLL and/or objects are presumed inconsistent with those of the server's library.

6. The method of claim 4 wherein the remote distributed clients belonging to the health-care provider field include nurses of varying types, physicians, social workers, therapists of several types, or dieticians providing service to a patient at home, a resident of a nursing home, or a patient at a physician's office remote from a medical complex.

* * * * *